| (12) | United States Patent | (10) Patent No.: | US 9,662,663 B2 |
|---|---|---|---|
| | Kanai et al. | (45) Date of Patent: | May 30, 2017 |

(54) MAGNETIC PARTICLE MANIPULATION APPARATUS

(71) Applicant: SHIMADZU CORPORATION, Kyoto (JP)

(72) Inventors: Masaki Kanai, Nara (JP); Tetsuo Ohashi, Osaka (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/972,102

(22) Filed: Dec. 17, 2015

(65) Prior Publication Data

US 2016/0180998 A1  Jun. 23, 2016

(30) Foreign Application Priority Data

Dec. 22, 2014 (JP) ................. 2014-259012

(51) Int. Cl.

| B03C 1/28 | (2006.01) |
| B03C 1/03 | (2006.01) |
| B01L 9/06 | (2006.01) |
| G01N 35/00 | (2006.01) |
| B03C 1/033 | (2006.01) |
| B01L 3/00 | (2006.01) |
| H01F 7/02 | (2006.01) |

(52) U.S. Cl.
CPC .............. *B03C 1/288* (2013.01); *B01L 3/502* (2013.01); *B01L 9/06* (2013.01); *B03C 1/0332* (2013.01); *G01N 35/0098* (2013.01); *B01L 2200/0668* (2013.01); *B01L 2200/0673* (2013.01); *B01L 2300/087* (2013.01); *B01L 2300/0832* (2013.01); *B01L 2400/043* (2013.01); *B03C 2201/18* (2013.01); *B03C 2201/26* (2013.01); *H01F 7/0273* (2013.01)

(58) Field of Classification Search
CPC ... B03C 1/288; B03C 1/0332; B03C 2201/26; B03C 2201/18; B01L 9/06; B01L 3/502; B01L 2200/0668; B01L 2200/0673; B01L 2300/0832; B01L 2300/087; B01L 2400/043; G01N 35/0098
See application file for complete search history.

(56) References Cited

FOREIGN PATENT DOCUMENTS

| CN | 103269787 | 8/2013 |
| WO | 97/44671 | 11/1997 |
| WO | 2008097896 | 8/2008 |
| WO | 2012/086243 | 6/2012 |

*Primary Examiner* — David A Reifsnyder

(74) *Attorney, Agent, or Firm* — Jianq Chyun IP Office

(57) ABSTRACT

The invention relates to a magnetic particle manipulation apparatus for moving magnetic particles within a tubular device, wherein the tubular device includes a gel-like medium layer and a liquid layer alternately stacked within a vessel and is filled with the magnetic particles. The magnetic particle manipulation apparatus of the invention includes a vessel holding portion, a vessel pressing portion and a magnetic field applying portion. The magnetic field applying portion includes a magnetic force source. At least one of the magnetic field applying portion and the vessel holding portion includes a moving mechanism capable of moving the magnetic force source. The vessel is pressed by the vessel pressing portion. The magnetic force source is moved relatively to the vessel holding portion by the moving mechanism, so as to move the magnetic particles.

5 Claims, 8 Drawing Sheets

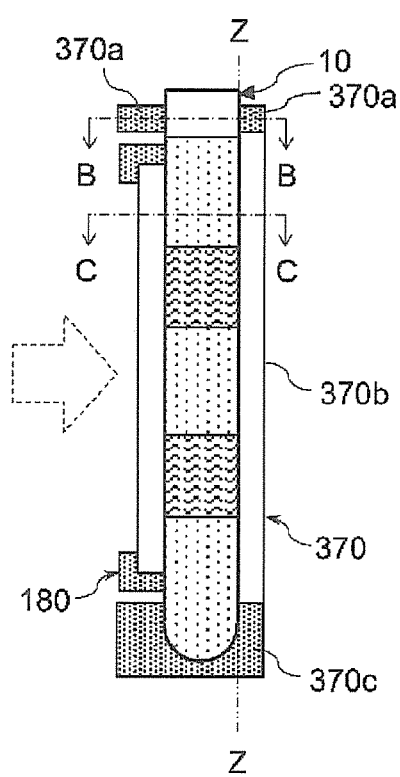
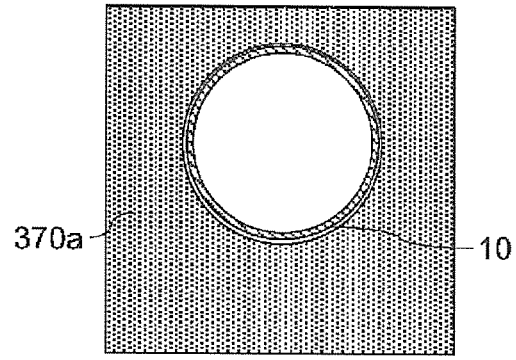
FIG. 4B
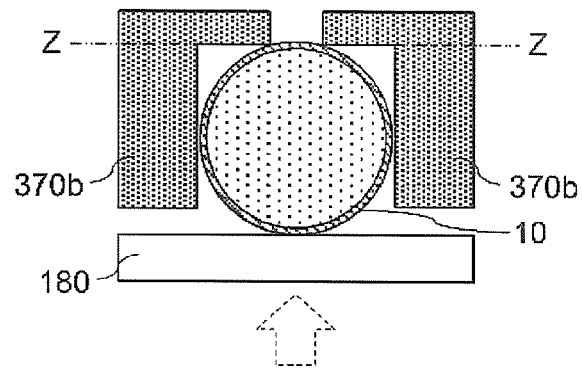
FIG. 4C
FIG. 4A

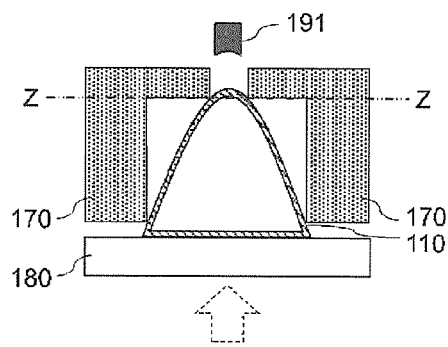 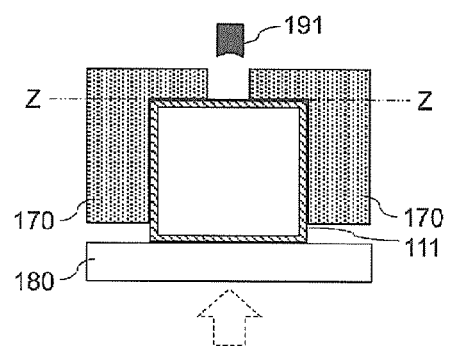
FIG. 9A    FIG. 9B
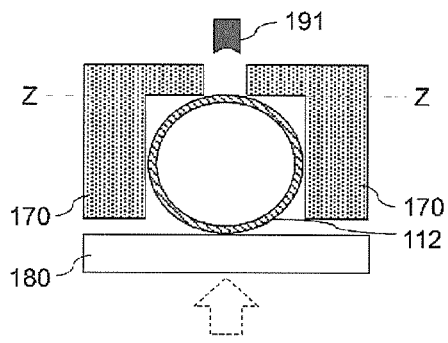
FIG. 9C
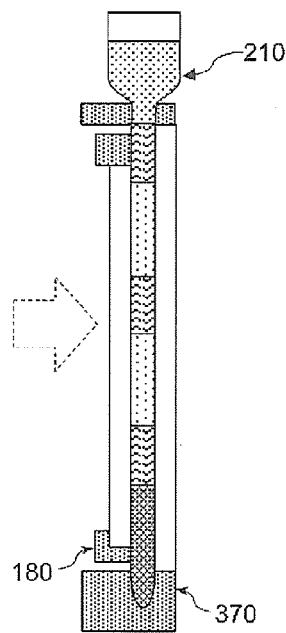
FIG. 10

MAGNETIC PARTICLE MANIPULATION APPARATUS

CROSS-REFERENCE TO RELATED APPLICATIONS

This application claims the priority benefit of Japan application serial no. 2014-259012, filed on Dec. 22, 2014. The entirety of the above-mentioned patent application is hereby incorporated by reference herein and made a part of this specification.

BACKGROUND OF THE INVENTION

Field of the Invention

The invention relates to a magnetic particle manipulation apparatus for performing chemical operations such as separation, extraction, purification, reaction, and so on of a target substance using magnetic particles.

Description of the Related Art

In monitoring or the like for medical examination, food safety and health management, and environmental conservation, a target substance is required to be extracted from a sample containing a great variety of impurities and then subjected to detection or reaction. For example, in medical examination, it is necessary to detect, identify and quantify nucleic acids, proteins, sugars, lipids, bacteria, viruses, radioactive substances and so on contained in blood, serum, cells, urine, feces and so on that are obtained by separation from animals and plants. During the examination of these substances, in order to eliminate bad influences of the background or the like caused by the impurities, it will sometimes be necessary to separate and purify the target substance.

In order to separate and purify a target substance in a sample, a method of using magnetic particles has been developed and put into practice which imparts chemical affinity with the target substance or a molecular recognition function to a surface of a magnetic having a particle diameter of around 0.5 µm to more than 10 µm. In this method, after the target substance is fixed to the surface of the magnetic particles, the magnetic particles are separated and recovered from the liquid phase by magnetic field manipulation; if necessary, steps of dispersing the recovered magnetic particles in the liquid phase of a cleaning solution or the like and separating and recovering the magnetic particles from the liquid phase are repeated. Thereafter, by dispersion of the magnetic particles in an eluent, the target substance fixed to the magnetic particles is released into the eluent, and the target substance in the eluent is recovered. By using magnetic particles, recovery of a target substance by means of a magnet becomes possible. Therefore, the method is advantageous in terms of automation of chemical extraction and purification.

The magnetic particles to which the target substance can be selectively fixed are commercially available as a part of a separation and purification kit. The kit includes a plurality of reagents placed in separate vessels. When the kit is in use, the user aliquots and dispenses the reagents with a pipette or the like. An apparatus for automating the pipetting operation or magnetic field manipulation is also commercially available (Patent Document 1). On the other hand, a method is proposed in which, instead of performing the pipetting operation, a tubular device in which a liquid layer such as a solution/fixing solution, a cleaning solution, an eluent or the like and a gel-like medium layer are alternately stacked with each other within a tubular vessel such as a capillary or the like is used, and the magnetic particles are moved within this device along a longitudinal direction of the vessel, thereby separating and purifying the target substance (Patent Document 2).

PRIOR-ART DOCUMENTS

Patent Documents

Patent Document 1: WO 97/44671.
Patent Document 2: WO 2012/086243.

SUMMARY OF THE INVENTION

In the case of using the tubular device, since a series of operations can be implemented in a closed system, the danger of contamination is reduced as compared to the pipetting operation performed in an open system. Patent Document 2 describes that, by movement of a magnetic force source such as a permanent magnet or a moving magnet plate and so on in a uniaxial direction, the magnetic particles are moved within the tubular device along the longitudinal direction of the vessel. The magnetic particles are gathered on an inner wall surface of the vessel in the vicinity of the magnetic force source due to the effect of a magnetic field, and then move along the longitudinal direction of the vessel in accordance with a magnetic field variation.

However, in the method of moving the magnetic force source in the uniaxial direction as described in Patent Document 2, even if a straight tubular vessel is used, the magnetic particles that should be moved sometimes cannot follow the variation in the magnetic field and may remain within the vessel, especially in the gel-like medium layer.

A force received by the magnetic particles from the magnetic force source (magnet) disposed outside the tubular device is considerably influenced by a distance between the magnetic force source and the magnetic particles, i.e., a distance between the magnetic force source and the inner wall surface of the vessel. The greater this distance, the more unlikely the magnetic particles are attracted by the magnetic field. Therefore, it becomes difficult to move the magnetic particles to pass them through the liquid layer or the gel-like medium layer. Because the force received by the magnetic particles from the magnetic force source will considerably change when the distance between the magnetic force source and the magnetic particles differs even by approximately 100 µm, it is required that the above-mentioned distance be precisely controlled. Particularly in the case of using the tubular device, because the gel-like medium has high viscosity and the magnetic particles hardly pass through the gel-like medium layer, compared to the pipetting operation using no gel-like medium, higher precision is required for the distance between the magnetic force source and the magnetic particles.

In view of the above, the invention provides a magnetic particle manipulation apparatus that includes a mechanism moving the magnetic force source relatively to the vessel in the uniaxial direction and that is capable of smoothly moving the magnetic particles within the tubular device in which the gel-like medium layer and the liquid layer are alternately stacked with each other.

It may be considered to control the distance between the magnetic force source and the magnetic particles so as to smoothly move the magnetic particles within the tubular device. However, as mentioned above, it is not sufficient to only move the magnetic force source in the uniaxial direction. The inventors have studied the reason and found out that even in a straight tubular vessel, bending actually occurs, with the result that at places where the distance between the magnetic force source and the magnetic particles deviates from a predetermined value even slightly, movement of the magnetic particles becomes difficult. Moreover, bending of the vessel is conspicuous if the vessel is formed from a resin material such as polypropylene or polyethylene and so on into the straight tubular shape. Particularly, it is known that if the vessel has a non-circular cross section, stress and strain applied during the forming process are increased, so that the vessel is likely to bend. Although it is undoubtedly possible to make a more precise straight tubular vessel by adjusting forming conditions and processing conditions of the vessel, another problem is caused in which production cost of the device increases.

The inventors have discovered the following. In a magnetic particle manipulation apparatus including a vessel holding portion for holding the vessel, a vessel pressing portion for pressing the vessel to the vessel holding portion, and a magnetic field applying portion, the vessel holding portion has a receiving surface parallel to the uniaxial direction (a relative movement direction between the vessel and a magnetic force source). The vessel is pressed by the vessel pressing portion in a direction orthogonal to the uniaxial direction, such that the vessel is fixed onto the receiving surface. Thereby, bending of the vessel can be canceled, and a distance between the magnetic force source and an outer wall surface of the vessel can be kept constant. Accordingly, a distance between the magnetic force source and an inner wall surface of the vessel and a distance between the magnetic force source and the magnetic particles can be controlled. Particularly, if the vessel has a constant wall thickness on a side opposed to the magnetic force source, the distance between the magnetic force source and the magnetic particles can be kept constant. As a result, the magnetic particles are capable of smoothly moving in the gel-like medium layer and the liquid layer, particularly even in the gel-like medium layer having high viscosity.

That is, the invention relates to a magnetic particle manipulation apparatus for moving magnetic particles within a tubular device, wherein the tubular device includes a gel-like medium layer and a liquid layer alternately stacked with each other within a vessel and is filled with the magnetic particles. The magnetic particle manipulation apparatus of the invention includes a vessel holding portion for holding the vessel, a vessel pressing portion for pressing the vessel to the vessel holding portion, and a magnetic field applying portion, wherein the magnetic field applying portion includes a magnetic force source, and at least one of the magnetic field applying portion and the vessel holding portion includes a moving mechanism capable of moving the magnetic force source relatively to the vessel holding portion in a uniaxial direction. By pressing of the vessel in a direction orthogonal to the uniaxial direction by the vessel pressing portion, the vessel is fixed onto a receiving surface of the vessel holding portion parallel to the uniaxial direction. By movement of the magnetic force source relatively to the vessel holding portion in the uniaxial direction by means of the moving mechanism, the magnetic particles can be moved within the vessel in a longitudinal direction of the vessel.

In the invention, the vessel is preferably held in a manner that the longitudinal direction of the vessel is parallel to the uniaxial direction. In this case, the distance between the magnetic force source and the magnetic particles can be more precisely controlled.

In the invention, the vessel holding portion is preferably disposed between the vessel pressing portion and the magnetic field applying portion. For example, if the magnetic field applying portion, the vessel pressing portion and the vessel holding portion are arranged in this order, there is a fear that the vessel pressing portion may obstruct magnetic lines from the magnetic force source included in the magnetic field applying portion. There is also a fear that when the vessel pressing portion presses the vessel, the magnetic field applying portion becomes an obstacle so that operability is reduced. On the other hand, if the vessel holding portion is disposed between the vessel pressing portion and the magnetic field applying portion, such problems do not occur. Therefore, excellent operability is provided.

In the invention, the vessel holding portion preferably has a gap in a portion equivalent to a movement region of the magnetic force source within a portion opposed to the magnetic force source. By formation of the gap such as a slit or the like in the vessel holding portion, interference of the magnetic lines from the magnetic force source can be suppressed.

In the invention, the vessel holding portion preferably includes a nonmagnetic material so as not to obstruct the magnetic lines from the magnetic force source.

According to the apparatus of the invention, since the distance between the magnetic force source and the outer wall surface of the vessel can be kept constant, the distance between the magnetic force source and the inner wall surface of the vessel and the distance between the magnetic force source and the magnetic particles can be controlled. Particularly, if the vessel has a constant wall thickness on the side opposed to the magnetic force source, the distance between the magnetic force source and the magnetic particles can be kept constant. As a result, the magnetic particles are capable of smoothly moving within the tubular device in which the gel-like medium layer and the liquid layer are alternately stacked with each other. Accordingly, improvement in efficiency, yield or examination precision of chemical operations can be expected.

BRIEF DESCRIPTION OF THE DRAWINGS

FIGS. 4A to 4C are schematic views illustrating an embodiment of the vessel holding portion having a hole.

FIGS. 9A to 9C are schematic views illustrating another embodiment of the vessel.

FIG. 10 is a schematic cross-sectional view illustrating still another embodiment of the vessel.

DESCRIPTION OF EXEMPLARY EMBODIMENTS

Prior to the description of the magnetic particle manipulation apparatus of the invention, a method of manipulating magnetic particles in a tubular device used in the apparatus is described.

[Method of Manipulating Magnetic Particles]

Figure 1A:
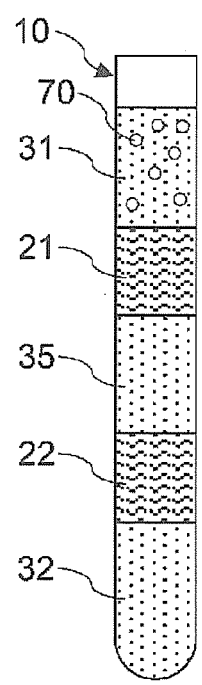
FIGS. 1A to 1C are schematic cross-sectional views illustrating an example of a tubular device in which magnetic particles are manipulated.
Figure 1B:
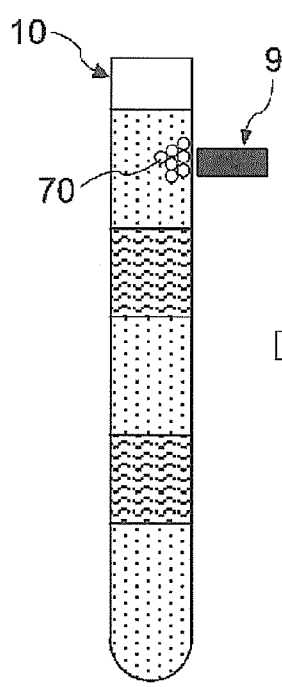
Figure 1C:
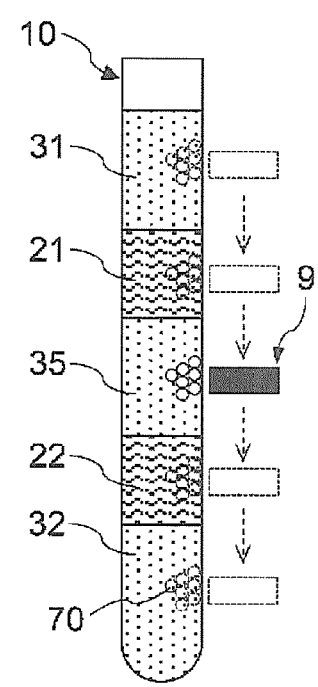

FIGS. 1A to 1C are schematic cross-sectional views illustrating an example of a tubular device in which magnetic particles are manipulated. As shown in FIG. 1A, in this device, liquid layers 32, 35 and 31 are alternately stacked with gel-like medium layers 22 and 21 within a tubular vessel 10 from a bottom surface side of the vessel. The gel-like medium is not miscible with the liquid in the adjacent liquid layer, and is insoluble or hardly soluble in these liquids.

In FIG. 1A, a plurality of magnetic particles 70 are contained in the liquid layer 31 at an upper portion of the vessel. The magnetic particles 70 are particles specifically capable of fixing thereon or therein a target substance such as a nucleic acid or an antigen. By dispersion of the magnetic particles 70 in the liquid layer 31, the target substance contained in the liquid layer 31 is selectively fixed to the magnetic particles 70.

The method of fixing the target substance to the magnetic particles is not particularly limited. Various well-known immobilization mechanisms such as physisorption, chemisorption and so on are applicable. For example, by various intermolecular forces such as van der Waals forces, hydrogen bonding, hydrophobic interaction, ion-ion interaction, π-π stacking and so on, the target substance is fixed to the surface or the inside of the particles.

The particle diameter of the magnetic particles is preferably 1 mm or less, more preferably 0.1 μm to 500 μm. The shape of the particles is desirably a spherical shape having a uniform particle diameter. However, as long as particle manipulation is possible, the particles may have an irregular shape and a particle diameter distribution to some extent. The particles may be composed of a single substance or a plurality of components.

The magnetic particles may be formed from only the magnetic, but those coated with a coating for specifically fixing the target substance to a surface of the magnetic are preferably used. Examples of the magnetic include iron, cobalt, nickel, and compounds thereof, oxides thereof and alloys thereof, etc. Specific examples include magnetite ($Fe_3O_4$), hematite ($Fe_2O_3$ or $\alpha\text{-}Fe_2O_3$), maghemite ($\gamma\text{-}Fe_2O_3$), titanomagnetite ($xFe_2TiO_4 \cdot (1-x)Fe_3O_4$), ilmenohematite ($xFeTiO_3 \cdot (1-x)Fe_2O_3$), pyrrhotite ($Fe_1\text{-}xS$ (x=0 to 0.13), e.g. $Fe_7S_8$ (x=0.13)), greigite ($Fe_3S_4$), geothite ($\alpha$-FeOOH), chromium oxide ($CrO_2$), permalloy, alnico magnet, stainless steel, samarium magnet, neodymium magnet, and barium magnet.

Examples of the target substance selectively fixed to the magnetic particles include organism-derived substances such as nucleic acids, proteins, sugars, lipids, antibodies, receptors, antigens, ligands and so on or cells themselves. If the target substance is an organism-derived substance, the target substance may be fixed to the inside or the surface of the particles by molecular recognition or the like. For example, if the target substance is a nucleic acid, magnetic particles having a silica coating applied to their surface are preferably used as the magnetic particles 70. If the target substance is an antibody (e.g., labeled antibody), a receptor, an antigen or a ligand and so on, the target substance can be selectively fixed to the particle surface by amino groups, carboxyl groups, epoxy groups, avidin, biotin, digoxigenin, protein A, protein G or the like on the particle surface. As the magnetic particles capable of selectively fixing a specific target substance, e.g., a commercial product such as Dynabeads® commercially available from Life Technologies, or MagExtractor™ commercially available from Toyobo Co., Ltd., or the like, can also be used.

As shown in FIG. 1B, when a magnet 9 as a magnetic force source is brought close to an outer wall surface of the vessel 10, the magnetic particles 70 to which the target substance is fixed are gathered on an inner wall surface of the vessel 10 in the vicinity of the magnet 9 due to the effect of a magnetic field. As shown in FIG. 1C, when the magnet 9 is moved in a longitudinal direction of the vessel 10 along the outer wall surface, in accordance with a magnetic field variation, the magnetic particles 70 also move along the longitudinal direction of the vessel 10 to the gel-like medium layer 21, the liquid layer 35, the gel-like medium layer 22 and the liquid layer 32 in sequence. A majority of the liquid physically attached around the magnetic particles 70 as droplets detaches from the particle surface when the particles enter the gel-like medium. Due to entry and movement of the particles into the gel-like medium layers 21 and 22, the gel-like medium is perforated, but holes of the gel-like medium are immediately closed due to a self-recovery effect by means of a restoring force of gel. Hence, the inflow of the liquid into the gel-like medium via through holes caused by the particles hardly occurs.

The magnetic particles 70 are dispersed within the liquid layers 35 and 31, and by contact of the magnetic particles with the liquids in the liquid layers, operations such as fixing of the target substance to the magnetic particles, cleaning for removing impurities attached to the surface of the magnetic particles, reaction of the target substance fixed to the magnetic particles, elution of the target substance fixed to the magnetic particles into the liquids and so on are performed.

For example, when the magnetic particles coated with a silica coating are used to perform separation and extraction of a nucleic acid, the magnetic particles 70 are dispersed in a liquid sample 31 containing a nucleic acid extraction liquid and the nucleic acid. After the nucleic acid is fixed to the surface of the magnetic particles 70, the magnetic particles 70 are moved into a cleaning solution 35. The magnetic particles 70 are dispersed in the cleaning solution 35 and have contaminating proteins or the like attached to their surface removed, and then the magnetic particles 70 are moved into the nucleic acid extraction liquid 32. By dispersion of the magnetic particles 70 in the nucleic acid extraction liquid 32, the nucleic acid fixed to the particle surface can be recovered in the nucleic acid extraction liquid 32. Moreover, although in FIGS. 1A to 1C, one liquid layer 35 is filled in the vessel 10 as the cleaning solution, the cleaning solution may include two layers or three or more layers. In addition, in a scope with no undesired obstruction being caused in purposes or uses of the separation, the cleaning solution can also be omitted.

In addition, if the substance selectively fixed to the magnetic particles is an antigen, the antigen contained in the liquid layer 31 as the first medium layer is fixed to the surface of the magnetic particles 70 coated with molecules capable of selectively immobilizing antigens such as protein G or protein A and so on. By dispersion of the magnetic particles within the liquid layer 35, the cleaning for removing the impurities attached to the particle surface is performed. By dispersion of the magnetic particles within the liquid layer 32 as the second medium layer, an antigen-antibody reaction between the antigen fixed to the particle surface and an antibody in the liquid layer 32, or release and elution of the target substance into the liquid layer 32, can be performed.

The above-mentioned particle manipulating method can be implemented in a closed system since there is no need to generate a liquid current by a pipette or the like. If the vessel is sealed and filled with the liquid, the gel-like medium and the magnetic particles, contamination from the outside can be prevented. Hence, the method is particularly useful in cases where manipulation is performed by fixing a target substance that easily decomposes, such as RNA, to the magnetic particles, or where a liquid that easily reacts with oxygen or the like in the air is used. When the vessel is to be made a closed system, the vessel can be sealed by a method of thermally fusing an opening portion of the vessel or by using an appropriate sealing means. If it is necessary to remove the particles after manipulation or the liquid after elution of the target substance from the vessel, it is preferred to removably seal the opening portion using a resin stopper or the like. In addition, like the device shown in FIGS. 1A to 1C, the liquid may be sealed and filled by arranging a gel layer or the like adjacent to the liquid.

The liquid filled into the vessel provides a place for performing chemical operations such as extraction, purification, reaction, separation, detection, analysis and so on of the target substance fixed to the surface of the magnetic particles. Although the type of the liquid is not particularly limited, a liquid that does not dissolve the gel-like medium is preferred. Hence, as the liquid, an aqueous solution or an aqueous liquid such as a mixed solution of water and an organic solvent is preferably used. The liquid may function as a mere medium for these chemical operations, and may also be directly involved in the chemical operations, or may contain a compound involved in the chemical operations as a component. The substance contained in the liquid can be exemplified by substances reacting with reactive substances fixed to the magnetic particles, substances further reacting with the substances fixed to the surface of the magnetic particles due to the reaction, reaction reagents, fluorescent substances, various buffers, surfactants, salts, and other various adjuvants, and organic solvents such as alcohol and so on. The aqueous liquid may be provided in an arbitrary form such as water, aqueous solution or aqueous suspension and so on.

In cases where the target substance contained in the liquid sample is fixed to the surface of the magnetic particles, the liquid sometimes contains, in addition to the target substance to be fixed to the surface of the magnetic particles, a great variety of impurities. The liquid sample may contain, e.g., biological specimens such as animal and plant tissues, body fluids, excreta and so on, and nucleic acid-containing materials such as cells, protozoa, fungi, bacteria, viruses and so on. The body fluids include blood, spinal fluid, saliva, milk and so on. The excreta include feces, urine, sweat and so on. The cells include white blood cells and platelets in blood, or exfoliated mucosal cells such as exfoliated oral mucosal cells, and white blood cells in saliva, and so on.

The liquid sample containing the target substance such as nucleic acids, antigens, antibodies and so on may also be prepared as, e.g., a mixture with a cell suspension, a homogenate or a cell lysate. If the target substance contained in an organism-derived sample such as blood or the like is fixed to the particle surface, the liquid sample is a mixture of the organism-derived sample such as blood or the like and a cell lysate (nucleic acid extraction liquid) for extracting the target substance from the organism-derived sample. The cell lysate contains a component capable of dissolving cells of a chaotropic substance or a surfactant and so on.

Examples of the cell lysate (nucleic acid extraction liquid) for nucleic acid extraction include a buffer solution containing chaotropic substances, chelating agents such as EDTA or the like, Tris-HCl and so on. In addition, the cell lysate can also contain a surfactant such as Triton X-100 or the like. Examples of the chaotropic substances include guanidine hydrochloride, guanidine isothiocyanate, potassium iodide, urea and so on. The cell lysate may also contain, in addition to the above, proteases such as Proteinase K or the like, or various buffers, salts, and other various adjuvants, and organic solvents such as alcohol and so on.

The cleaning solution may be a solution capable of releasing the components (e.g., proteins, saccharides, etc.) other than nucleic acids contained in the sample or reagents used in processes such as nucleic acid extraction into the cleaning solution while keeping the nucleic acids fixed to the particle surface. Examples of the cleaning solution include high-salt concentration aqueous solutions such as sodium chloride, potassium chloride, ammonium sulfate and so on, and alcohol aqueous solutions such as ethanol, isopropanol and so on.

As a nucleic acid eluent, water or a buffer solution containing a low concentration of salt can be used. Specifically, Tris buffer solutions, phosphate buffer solutions, distilled water and so on can be used, and 5 to 20 mM of a Tris buffer solution having a pH adjusted to 7 to 9 is generally used. By dispersion of the magnetic particles to which the nucleic acids are fixed in the eluent, the nucleic acids can be released and eluted into the nucleic acid eluent. The recovered nucleic acids are subjected to operations such as concentration or drying and hardening if necessary and then can be used for analysis or reaction and so on.

The gel-like medium filled in the vessel may be gelatinous or pasty before particle manipulation. The gel-like medium is insoluble or hardly soluble in the liquid in the adjacent liquid layer, and is preferably a chemically-inactive substance. Herein, "insoluble or hardly soluble in the liquid" means having solubility of roughly 100 ppm or less to the liquid at 25° C. The "chemically-inactive substance" refers to a substance having no chemical influence on the liquid layer, the magnetic particles or the substance fixed to the magnetic particles during the contact with the liquid layer or during the manipulation of the magnetic particles (i.e., manipulation to move the magnetic particles in the gel-like medium).

The material or composition and so on of the gel-like medium is not particularly limited, and the gel-like medium may be a physical gel or a chemical gel. For example, as described in WO 2012/086243, a water-insoluble or hardly water-soluble liquid substance is heated, and a gelling agent is added to the heated liquid substance. After the gelling agent is completely dissolved, the resultant is cooled at the sol-gel transition temperature or lower, thereby forming a physical gel.

The filling of the gel-like medium and the liquid into the vessel can be performed by an appropriate method. If a tubular vessel is used, it is preferred that prior to the filling, the opening on one end of the vessel is sealed, and the gel-like medium and the liquid are sequentially filled from the opening portion on the other end.

The amount of the gel-like medium and the liquid that can be filled in the vessel can be properly set according to the amount of the magnetic particles to be manipulated, or the type of manipulation, and so on. If a plurality of gel-like medium layers or liquid layers are provided in the vessel, the amount of each layer may be the same or different. The thickness of each layer can also be properly set. In view of operability and so on, the layer thickness is preferably approximately, e.g., 2 mm to 20 mm.

[Magnetic Particle Manipulation Apparatus]

Figures 2A, 2B, 2C, 2D:
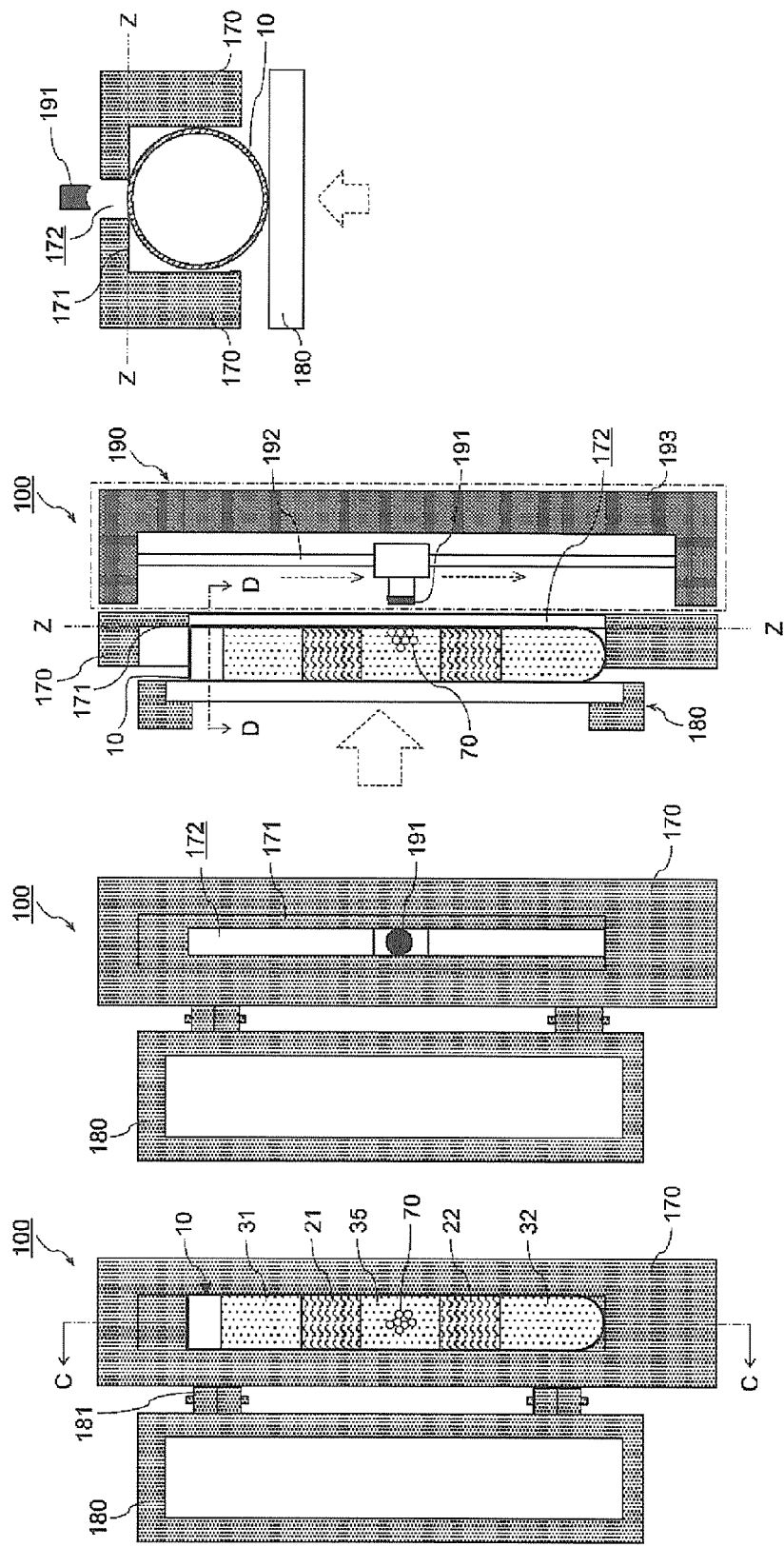
FIGS. 2A to 2D are schematic views illustrating an embodiment of a magnetic particle manipulation apparatus of the invention.

FIG. 2A is a schematic front view illustrating an embodiment of a magnetic particle manipulation apparatus of the invention. FIG. 2B is a schematic front view illustrating the magnetic particle manipulation apparatus while not holding the vessel. FIG. 2C is a cross-sectional view of the magnetic particle manipulation apparatus in which the vessel 10 is held by a vessel holding portion 170 and pressed by a vessel pressing portion 180, taken along line C-C of FIG. 2A. FIG. 2D is a cross-sectional view taken along line D-D of FIG. 2C.

A magnetic particle manipulation apparatus 100 shown in FIGS. 2A to 2D includes the vessel holding portion 170, the vessel pressing portion 180 and a magnetic field applying portion 190. In the embodiment shown in FIGS. 2A to 2D, the vessel holding portion 170 is disposed between the vessel pressing portion 180 and the magnetic field applying portion 190.

The magnetic field applying portion 190 includes a linear guide 192 fixed to a support plate 193, and a permanent magnet 191 slidably attached to the linear guide 192. The method of sliding the permanent magnet 191 is not particularly limited, and the permanent magnet 191 may be slid by a driving means such as a motor or the like or may be slid by hand. Since the permanent magnet 191 is capable of sliding on the linear guide 192, the magnetic field can be changed in a uniaxial direction. In the magnetic particle manipulation apparatus 100, by movement of the permanent magnet 191 in the uniaxial direction, the magnetic particles 70 can be moved within the vessel 10 in the longitudinal direction of the vessel 10.

Moreover, although in FIG. 2C, the permanent magnet 191 is moved in only one direction (downward direction), the permanent magnet 191 may also be moved back and forth in two directions (upward and downward directions).

The shape or size, material of the permanent magnet is not particularly limited as long as the permanent magnet is capable of the above-mentioned manipulation of magnetic particles. As the magnetic force source included in the magnetic field applying portion, in addition to the permanent magnet, an electromagnet can also be used. In addition, the magnetic field applying portion may include a plurality of magnetic force sources.

The vessel holding portion 170 is configured to be capable of holding the vessel 10. In the vessel 10, the liquid layers 31, 35, 32 and the gel-like medium layers 21 and 22 are alternately stacked with each other, and the magnetic particles 70 are further filled. The vessel 10 is detachably held by the vessel holding portion 170.

The method of holding the vessel 10 by the vessel holding portion 170 is not particularly limited. For example, a method may be mentioned in which a concave portion 171 extending in the longitudinal direction of the vessel 10 is formed in a wall surface of the vessel holding portion 170 on a side opposed to the permanent magnet 191, and the vessel 10 is held by fitting into the concave portion 171. An extension direction of the concave portion 171 is preferably parallel to a movement direction (uniaxial direction) of the permanent magnet 191. Accordingly, the vessel 10 can be held in a manner that the longitudinal direction of the vessel 10 is parallel to the movement direction of the permanent magnet 191.

FIGS. 2A to 2D show the example in which a bottom surface portion of the vessel 10 is fixed by a lower surface of the vessel holding portion 170. However, the bottom surface portion of the vessel 10 may not be fixed by the lower surface of the vessel holding portion 170. For example, it may be sufficient to only fit the vessel 10 into the concave portion 171. In addition, an upper surface of the vessel 10 may be fixed by the vessel holding portion.

A portion of the vessel holding portion 170 opposed to the permanent magnet 191 preferably has a slit 172 in a portion equivalent to a movement region of the permanent magnet 191. By formation of a gap such as a slit or the like in the vessel holding portion, interference of magnetic lines from the magnetic force source can be suppressed. Such slit is preferably continuously formed in the whole portion equivalent to the movement region of the magnetic force source such as the permanent magnet, but may also be formed discontinuous in the portion. The type of the gap is not limited to a slit, but may be a hole having a circular shape, an elliptical shape, or a polygonal shape and so on. In addition, as long as the vessel is held, the gap may also be formed in the portion other than the movement region of the magnetic force source.

The vessel pressing portion 180 is configured to be capable of pressing the vessel 10 to the vessel holding portion 170. In the embodiment shown in FIGS. 2A to 2D, the vessel pressing portion 180 is plate-like, and is rotatably connected to the vessel holding portion 170 via a hinge 181. The configuration of the vessel pressing portion is not particularly limited. The vessel pressing portion may be configured rotatable about a rotation axis composed of a hinge and so on, or may be configured movable parallel to while opposed to the vessel holding portion (movable in leftward and rightward directions in FIG. 2C).

As shown in FIGS. 2C and 2D, the vessel 10 is pressed in a direction orthogonal to the movement direction (uniaxial direction) of the permanent magnet 191 by the vessel pressing portion 180, and is fixed onto a receiving surface (Z-Z cross section in FIGS. 2C and 2D) of the vessel holding portion 170. Since the receiving surface of the vessel holding portion 170 is formed in the vessel holding portion 170 parallel to the uniaxial direction, even if the permanent magnet 191 moves in the uniaxial direction, a distance between the permanent magnet 191 and the outer wall surface of the vessel 10 is kept constant. Accordingly, a distance between the permanent magnet 191 and the inner wall surface of the vessel 10 or a distance between the permanent magnet 191 and the magnetic particles 70 can be controlled.

As a result, the magnetic particles 70 are capable of moving to the liquid layer 31, the gel-like medium layer 21, the liquid layer 35, the gel-like medium layer 22, and the liquid layer 32 in sequence. Particularly, the magnetic particles 70 are capable of smoothly moving even in the gel-like medium layers 21 and 22 having high viscosity.

Moreover, the receiving surface formed in the vessel holding portion refers to a surface passing through a contact point between the vessel and the vessel holding portion and parallel to the uniaxial direction. Accordingly, the receiving surface may be a surface that really exists in the vessel holding portion, or may be a virtual surface. In FIGS. 2C and 2D, the wall surface of the vessel holding portion 170 corresponds to the receiving surface.

If the vessel holding portion is capable of holding the vessel and resisting a pressing force from the vessel pressing portion, the material of the vessel holding portion is not particularly limited. However, from the viewpoint of not obstructing the magnetic lines from the magnetic force source, the vessel holding portion preferably includes a nonmagnetic material. Examples of such nonmagnetic material include nonmagnetic metals such as aluminum, copper and so on, resin, ceramic, glass and so on.

FIGS. 3A to 3E are schematic views illustrating another embodiment of the vessel holding portion. FIGS. 3A to 3E show cross sections orthogonal to the longitudinal direction of the vessel 10.

Figure 3A:
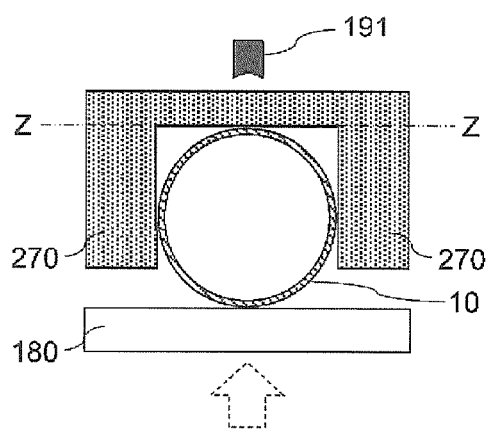
FIGS. 3A to 3E are schematic views illustrating another embodiment of the vessel holding portion.
Figure 3B:
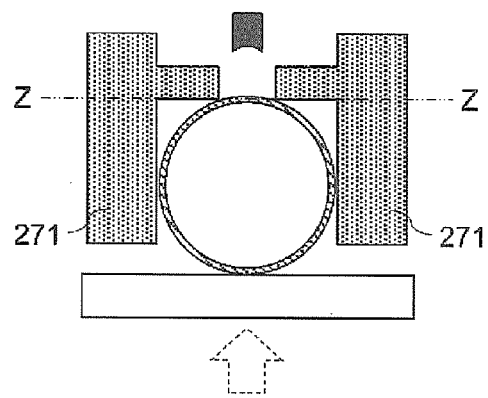

Like a vessel holding portion 270 shown in FIG. 3A, the vessel holding portion may not have a slit in the portion equivalent to the movement region of the permanent magnet 191 within the portion opposed to the permanent magnet 191. The vessel holding portion does not have to fix the vessel 10 by the wall surface opposed to the permanent magnet 191. Like a vessel holding portion 271 shown in FIG. 3B, the vessel holding portion may fix the vessel 10 by a protruding portion provided on both side surfaces. In FIG. 3A, the wall surface of the vessel holding portion 270 corresponds to the receiving surface; in FIG. 3B, the protruding portion provided on both side surfaces corresponds to the receiving surface.

Figure 3C:
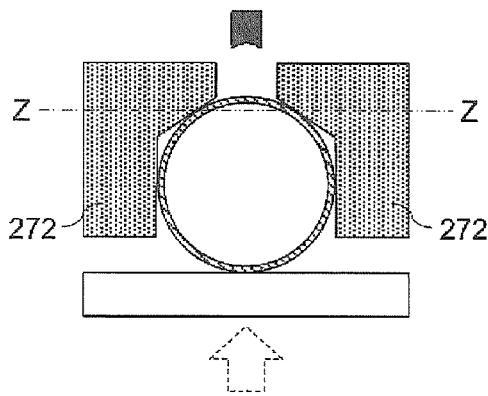
Figure 3D:
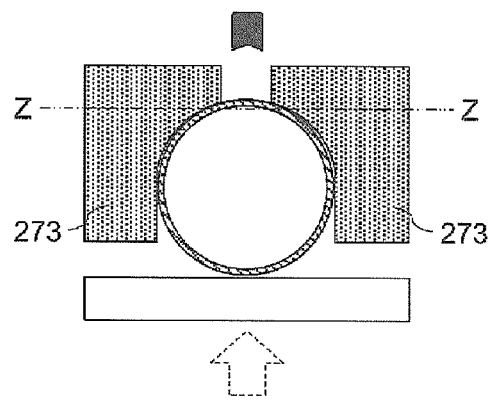
Figure 3E:
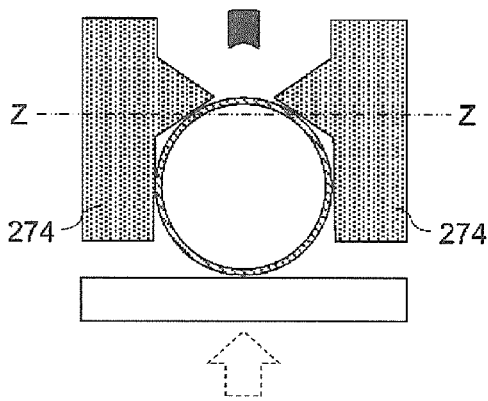

The vessel holding portion does not have to fix the vessel 10 by a wall surface parallel to the receiving surface. The vessel holding portion may, like a vessel holding portion 272 shown in FIG. 3C, fix the vessel 10 by a planar wall surface not parallel to the receiving surface, or may, like a vessel holding portion 273 shown in FIG. 3D, fix the vessel 10 by a curved wall surface. The respective wall surfaces may not have a slit formed therein. Furthermore, like a vessel holding portion 274 shown in FIG. 3E, the vessel holding portion may fix the vessel 10 by a protruding portion in various shapes. In FIGS. 3C to 3E, the receiving surface is a virtual surface formed of a set of contact points between the vessel holding portion and the vessel.

FIGS. 4A to 4C are schematic views illustrating an embodiment of the vessel holding portion having a hole. FIG. 4B is a cross-sectional view taken along line B-B of FIG. 4A, and FIG. 4C is a cross-sectional view taken along line C-C of FIG. 4A. Like a vessel holding portion 370 shown in FIGS. 4A to 4C, the vessel holding portion may have a hole allowing the vessel to pass therethrough. An upper surface 370a and a lower surface 370c of the vessel holding portion 370 are supported by a support portion 370b. In the upper surface 370a, a hole circular in cross section allowing the vessel 10 to pass therethrough is formed. In the lower surface 370c, a concave portion capable of holding the bottom surface portion of the vessel 10 is formed. By passing the vessel 10 through the hole of the upper surface 370a and arranging the bottom surface portion of the vessel 10 in the concave portion of the lower surface 370c, the longitudinal direction of the vessel 10 can be fixed parallel to the movement direction of the permanent magnet (not illustrated). Furthermore, by pressing of the vessel 10 by the vessel pressing portion 180, the vessel 10 is fixed onto a receiving surface of the support portion 370b of the vessel holding portion 370. Moreover, although FIG. 4A shows the example in which the lower surface 370c of the vessel holding portion 370 has a concave portion, the lower surface of the vessel holding portion may have a hole instead of a concave portion. In addition, there may be neither a concave portion nor a hole.

In the embodiment shown in FIGS. 4A to 4C, in the vessel holding portion 370, an intermediate face that has a hole allowing the vessel to pass therethrough, similarly to the upper surface 370a, may be provided between the upper surface 370a and the lower surface 370c. There may be one or a plurality of intermediate faces.

In addition, instead of the upper surface 370a or the intermediate face, a ring-shaped member may be provided. By passage of the vessel 10 through the ring, the longitudinal direction of the vessel 10 can also be fixed parallel to the movement direction of the permanent magnet.

Figure 5:
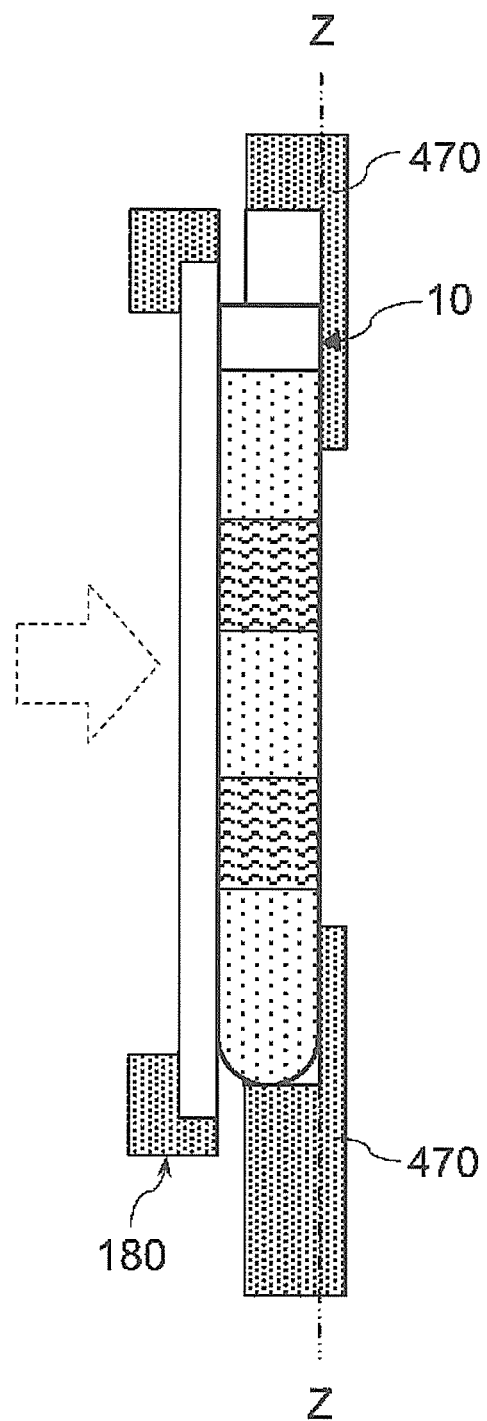
FIG. 5 is a schematic cross-sectional view illustrating still another embodiment of the vessel holding portion.

FIG. 5 is a schematic cross-sectional view illustrating still another embodiment of the vessel holding portion. In the embodiment shown in FIG. 5, a vessel holding portion 470 does not fix the entire surface of the vessel 10 pressed by the vessel pressing portion 180, but fixes upper and lower portions of the vessel 10. In the invention, from the viewpoint of keeping a constant distance between the magnetic force source and the outer wall surface of the vessel, the vessel holding portion preferably fixes the entire surface of the vessel opposed to the magnetic force source. However, as shown in FIG. 5, the vessel holding portion may also include portions that do not fix the vessel.

The material of the vessel pressing portion is not particularly limited, but is preferably a nonmagnetic material, similarly to the vessel holding portion. The material of the vessel pressing portion may be the same as or different from that of the vessel holding portion. In the vessel pressing portion, at least the portion for pressing the vessel preferably includes a transparent material. By use of the transparent material for the material of the portion, movement of the magnetic particles within the vessel can be observed, and problems such as residual magnetic particles in the vessel can be easily discovered. Particularly, if an optical measurement is performed during or after particle manipulation, the optical measurement can be performed while the vessel is pressed by the vessel pressing portion. As the transparent material, resins such as thermoplastic resin, thermosetting resin, photocurable resin and so on, glass and so on can be properly used.

Figure 6A:
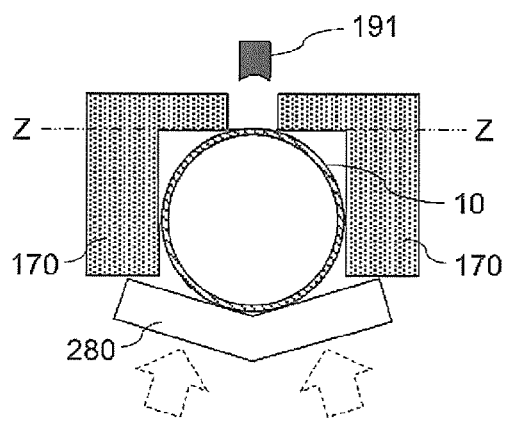
FIGS. 6A to 6C are schematic views illustrating another embodiment of the vessel pressing portion.
Figure 6B:
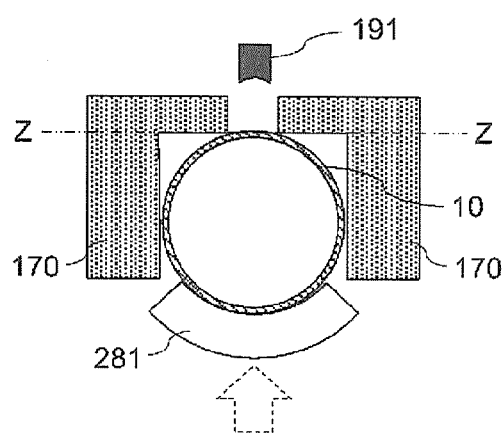
Figure 6C:
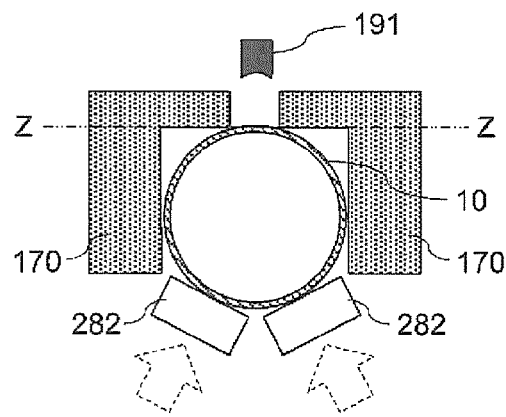

FIGS. 6A to 6C are schematic views illustrating another embodiment of the vessel pressing portion. FIGS. 6A to 6C show cross sections orthogonal to the longitudinal direction of the vessel 10. The vessel pressing portion may, like a vessel pressing portion 280 shown in FIG. 6A, press the vessel 10 by two or more faces, or may, like a vessel pressing portion 281 shown in FIG. 6B, press the vessel 10 along a curved surface. Furthermore, like a vessel pressing portion 282 shown in FIG. 6C, the vessel pressing portion may include a plurality of members.

Figure 7:
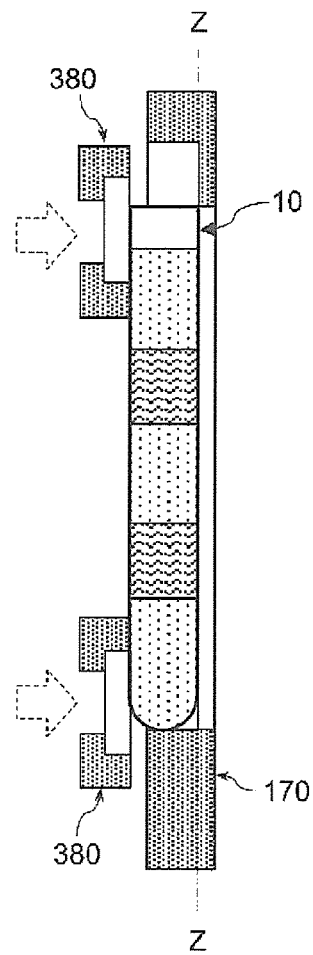
FIG. 7 is a schematic view illustrating still another embodiment of the vessel pressing portion.

FIG. 7 is a schematic view illustrating still another embodiment of the vessel pressing portion. In the embodiment shown in FIG. 7, a vessel pressing portion 380 does not press the entire surface of the vessel 10, but presses the upper and lower portions of the vessel 10. In the invention, from the viewpoint of keeping a constant distance between the magnetic force source and the outer wall surface of the vessel, the vessel pressing portion preferably presses the entire surface of the vessel. However, as shown in FIG. 7, the vessel pressing portion may also include portions that do not press the vessel. In addition, the vessel holding portion 470 shown in FIG. 5 and the vessel pressing portion 380 shown in FIG. 7 may be combined.

Figure 8:
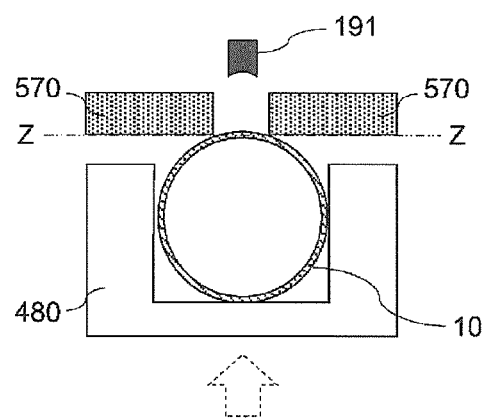
FIG. 8 is a schematic view illustrating another embodiment of the vessel holding portion and the vessel pressing portion.

FIG. 8 is a schematic view illustrating another embodiment of the vessel holding portion and the vessel pressing portion. As shown in FIG. 8, no concave portion is formed in a vessel holding portion 570 but a concave portion may be formed in the vessel pressing portion. A concave portion may be formed in neither of or both of the vessel holding portion and the vessel pressing portion. If a concave portion is formed in at least one of or both of the vessel holding portion and the vessel pressing portion, the shape of the concave portion is not particularly limited, but may be, e.g., a curved shape along the shape of the vessel. Moreover, in the embodiment shown in FIG. 8, the vessel holding portion 570 has a slit. However, the vessel holding portion may not have a slit.

Furthermore, a curved member like the vessel pressing portion 281 shown in FIG. 6B may be used as the vessel holding portion, and the vessel 10 may be interposed between two curved members.

In this way, by pressing of the vessel in the direction orthogonal to the uniaxial direction by the vessel pressing portion, as long as the vessel is fixed on the receiving surface parallel to the uniaxial direction, the shapes of the vessel holding portion and the vessel pressing portion are not particularly limited, but can be shapes in arbitrary combination.

As described above, in the invention, particle manipulation is performed in the liquid and the gel-like medium filled in the tubular vessel. If the magnetic particles are movable within the vessel, and the liquid and the gel-like medium can be held within the vessel, the material of the vessel is not particularly limited. In order to move the magnetic particles within the vessel by magnetic field manipulation from outside the vessel, a magnetic permeable material such as plastic or the like is preferred. Examples thereof include resin materials such as: polyolefins such as polypropylene or polyethylene and so on, fluorine-based resins such as tetrafluoroethylene and so on, polyvinyl chloride, polystyrene, polycarbonate, cyclic polyolefins and so on. These resin materials are so soft that the vessel may easily bend. However, by use of the magnetic particle manipulation apparatus of the invention, the distance between the magnetic force source and the outer wall surface of the vessel can be kept constant. As the material of the vessel, in addition to the above-mentioned materials, ceramic, glass, silicone, nonmagnetic metals and so on may also be used. In order to improve water repellency of the inner wall surface of the vessel, coating by means of fluorine-based resins or silicone and so on may be performed.

As long as the vessel is tubular, the shape of the vessel is not particularly limited. The cross-sectional shape of the vessel may be, in addition to the circular shape as in the vessel 10 shown in FIG. 2D and so on, a non-circular shape. Examples thereof include a shape formed by combining a straight line portion with a curved portion as in a vessel 110 shown in FIG. 9A, a polygonal shape as in a vessel 111 shown in FIG. 9B, and an elliptical shape as in a vessel 112 shown in FIG. 9C, and so on. If the vessel includes a resin material and has a non-circular cross-sectional shape, the vessel is very likely to bend. However, by use of the magnetic particle manipulation apparatus of the invention, the distance between the magnetic force source and the outer wall surface of the vessel can be kept constant. Moreover, if the cross-sectional shape of the vessel include a straight line portion, the straight line portion may be opposed to the permanent magnet 191, but is preferably opposed to the vessel pressing portion 180 as shown in FIGS. 9A and 9B. In this case, since the force from the vessel pressing portion is transmitted equally throughout the straight line portion of the vessel, the vessel will be easily pressed.

The vessel does not necessarily have a straight tubular shape. When seen along the longitudinal direction of the tube, there may be existing portions having larger diameters or portions having smaller diameters. For example, like the shape of a vessel 210 shown in FIG. 10, the upper portion has larger diameters and the lower portion has smaller diameters. If the vessel has such a shape, by use of the vessel holding portion 370 shown in FIGS. 4A to 4C, the vessel 210 can be fixed by using a border between the portion having larger diameters and the portion having smaller diameters as a supporting point.

The wall thickness of the vessel, i.e., a difference between an outer diameter and an inner diameter of the vessel, is not particularly limited. However, if the vessel has a constant wall thickness on the side opposed to the magnetic force source, the distance between the magnetic force source and the inner wall surface of the vessel can be kept constant, and thus the distance between the magnetic force source and the magnetic particles can be kept constant. In addition, since it is more difficult for the magnetic particles to pass through the gel-like medium layer than through the liquid layer, the distance between the magnetic force source and the magnetic particles is preferably constant at least in the portion filled with the gel-like medium layer. In view of the above, on the side opposed to the magnetic force source, the wall thickness of the vessel is preferably constant at least in the portion filled with the gel-like medium layer, and is more preferably constant in all portions. Furthermore, it is particularly preferred that the wall thickness of the entire vessel be constant.

The shape of the vessel may be, e.g., a straight tubular structure (capillary) having an inner diameter of approximately 1 mm to 2 mm and a length of approximately 50 mm to 200 mm. The inner diameter or the length of the tube may be properly selected according to the amount of the substance to be processed, the amount of the magnetic particles and so on.

During or after particle manipulation, in cases where an optical measurement of such as absorbance, fluorescence, chemiluminescence, bioluminescence, refractive index variation and so on is performed, or where light illumination is performed, a vessel having light transmissivity is preferably used. In addition, the vessel is preferably light transmissive also because the state of particle manipulation within the vessel can be observed by eyes. On the other hand, if it is necessary to shield the liquid or the magnetic particles and so on, a vessel having light shielding property and having no light transmissivity is preferably used. Depending on intended use and so on, a vessel having both a light transmissive portion and a light shielding portion can also be used.

The magnetic particle manipulation apparatus of the invention is not limited to the configuration described in the above embodiments, but can adopt various configurations.

The orientation of holding the vessel is not particularly limited. In addition to that the vessel is held with its longitudinal direction turned vertical, the vessel may also be held with its longitudinal direction turned, e.g., horizontal or oblique.

The method of changing the magnetic field along the longitudinal direction of the vessel is not limited to the configuration as shown in FIG. 2C in which the magnetic field applying portion includes the moving mechanism such as the linear guide or the like, and the magnetic force source is moved in the uniaxial direction, but may be a configuration in which the vessel holding portion includes the moving mechanism such as the linear guide or the like, and the vessel holding portion is moved in the uniaxial direction. In other words, it is satisfactory as long as one of the vessel holding portion and the magnetic field applying portion includes a moving mechanism capable of moving the magnetic force source relatively to the vessel holding portion in the uniaxial direction. In addition, the vessel holding portion and the magnetic field applying portion may both include the above-mentioned moving mechanism so as to move both the magnetic force source and the vessel holding portion.

In the invention, the vessel holding portion is preferably disposed between the vessel pressing portion and the magnetic field applying portion. However, the magnetic field applying portion, the vessel pressing portion and the vessel holding portion may be also arranged in this order.

The vessel holding portion and the vessel pressing portion do not have to be respectively fixed to the apparatus, but may also be detachable.

The above embodiments have described the example in which one vessel is held by the vessel holding portion and is fixed onto the receiving surface by the vessel pressing portion. In the invention, a plurality of vessels may be held by the vessel holding portion and fixed onto the same receiving surface by the vessel pressing portion. In that case, the magnetic field applying portion includes magnetic force sources respectively opposed to the vessels. In addition, the vessel pressing portion may be configured to be capable of pressing each vessel individually, or may be configured to be capable of pressing all the vessels by one face. Furthermore, if a plurality of vessels are held, a plurality of vessel holding portions may be provided in a manner that their respective receiving surfaces are arranged in parallel.

What is claimed is:

1. A magnetic particle manipulation apparatus for moving magnetic particles within a tubular device, wherein the tubular device comprises a gel-like medium layer and a liquid layer alternately stacked within a vessel and is filled with the magnetic particles, the magnetic particle manipulation apparatus comprising:
    a vessel holding portion for holding the vessel;
    a vessel pressing portion for pressing the vessel to the vessel holding portion; and
    a magnetic field applying portion, wherein
    the magnetic field applying portion comprises a magnetic force source;
    at least one of the vessel holding portion and the magnetic field applying portion comprises a moving mechanism moving the magnetic force source relatively to the vessel holding portion in a uniaxial direction;
    the vessel is pressed by the vessel pressing portion in a direction orthogonal to the uniaxial direction, such that the vessel is fixed onto a receiving surface of the vessel holding portion parallel to the uniaxial direction; and
    the magnetic force source is moved relatively to the vessel holding portion in the uniaxial direction by the moving mechanism, so as to move the magnetic particles within the vessel in a longitudinal direction of the vessel.

2. The magnetic particle manipulation apparatus according to claim 1, wherein the vessel is held in a manner that the longitudinal direction of the vessel is parallel to the uniaxial direction.

3. The magnetic particle manipulation apparatus according to claim 1, wherein the vessel holding portion is disposed between the vessel pressing portion and the magnetic field applying portion.

4. The magnetic particle manipulation apparatus according to claim 1, wherein the vessel holding portion has a gap in a portion equivalent to a movement region of the magnetic force source within a portion opposed to the magnetic force source.

5. The magnetic particle manipulation apparatus according to claim 1, wherein the vessel holding portion comprises a nonmagnetic material.

* * * * *